US007221765B2

(12) United States Patent

Chalupper et al.

(10) Patent No.: US 7,221,765 B2
(45) Date of Patent: May 22, 2007

(54) SYSTEM AND METHOD FOR INDIVIDUALIZED TRAINING OF HEARING AID USERS

(75) Inventors: Josef Chalupper, Paunzhausen (DE); Reinier Kortekaas, Erlangen (DE)

(73) Assignee: Siemens Audiologische Technik GmbH, Erlangen (DE)

( * ) Notice: Subject to any disclaimer, the term of this patent is extended or adjusted under 35 U.S.C. 154(b) by 644 days.

(21) Appl. No.: 10/408,948

(22) Filed: Apr. 8, 2003

(65) Prior Publication Data

US 2003/0194095 A1 Oct. 16, 2003

(30) Foreign Application Priority Data

Apr. 12, 2002 (EP) .................................. 02008405

(51) Int. Cl.

*H04R 29/00* (2006.01)
*H04R 5/00* (2006.01)
*H04R 25/00* (2006.01)
*A61B 5/12* (2006.01)
*A61B 5/00* (2006.01)
*G09B 21/00* (2006.01)

(52) U.S. Cl. ....................... 381/60; 381/23.1; 381/312; 73/585; 600/559; 434/112

(58) Field of Classification Search .................. 381/60; 73/585; 600/559

See application file for complete search history.

(56) References Cited

U.S. PATENT DOCUMENTS 6,322,521 B1 * 11/2001 Hou ........................... 600/559

FOREIGN PATENT DOCUMENTS

| | | |
|---|---|---|
| WO | WO 97/17819 | 5/1997 |
| WO | WO 00/64350 | 11/2000 |
| WO | WO 01/15043 | 3/2001 |
| WO | WO 01/52737 | 7/2001 |
| WO | WO 02/35884 | 5/2002 |

OTHER PUBLICATIONS

Hoag, Douglas, System and Method for Online Medical Data Managment and Training, Mar. 1, 2001, WO 01/15043.*

* cited by examiner

*Primary Examiner*—Vivian Chin
*Assistant Examiner*—Douglas Suthers
(74) *Attorney, Agent, or Firm*—Schiff Hardin, LLP

(57) ABSTRACT

In a method for individualized training of hearing aid users a number of hearing training courses are stored in a databank. An individual user profile is acquired in a training device. A transmission of the hearing training data from the databank to the training device and/or vice versa ensues via a data network before or during the implementation of the hearing training. The training thus ensues adapted to the respective user profile by means of one or more individualized hearing training courses.

11 Claims, 1 Drawing Sheet

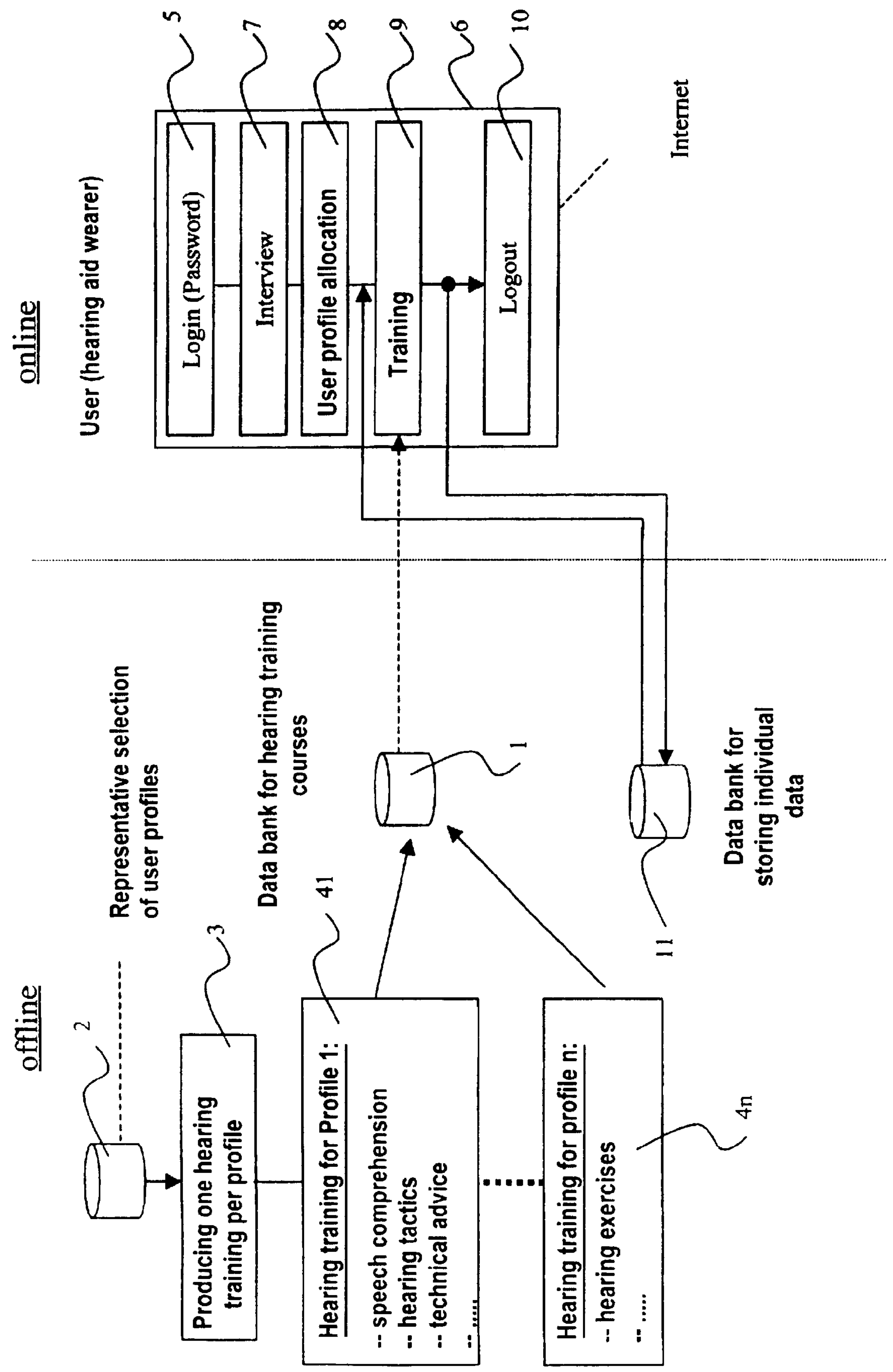
online
User (hearing aid wearer)
Login (Password)
Interview
User profile allocation
Training
Logout
Internet
5
7
8
9
6
10
offline
Representative selection
of user profiles
Data bank for hearing training
courses
Data bank for
storing individual
data
Producing one hearing
training per profile
Hearing training for Profile 1:
-- speech comprehension
-- hearing tactics
-- technical advice
-- .....
Hearing training for profile n:
-- hearing exercises
-- .....
1
2
3
41
4n
11

SYSTEM AND METHOD FOR INDIVIDUALIZED TRAINING OF HEARING AID USERS

BACKGROUND OF THE INVENTION

1. Field of the Invention

The present invention is directed to a system for training hearing aid users, having a databank for storing a number of hearing training courses and a training device for acquiring a user profile and for implementing one of the hearing training courses according to the user profile. The present invention is directed to a method for the implementation of such training.

2. Description of the Prior Art

In order to be able to optimally use a technical product, for example a hearing aid, one usually must first learn how to interact with it. This can occur by means of training, a hearing training in the present case. As used herein hearing training means all processes, methods and measures that can contribute to the hearing aid user getting a greater benefit from the hearing aid (greater satisfaction, higher speech comprehension, etc.). In addition to hearing training in the narrower sense, for example, hearing training also include hearing tactics, acceptance training, technical advice, and changes to the hearing aid settings. In order to be able to implement such training in a suitable way, it must be matched to an individual's prerequisites and needs. These prerequisites and needs represent the individual profile of the user. Parameters of such a profile are, for example, education, experience, time available for learning, expectations and goals with respect to the product and the like. The user profile may change during the training time. Changes particularly derive due to acclimatization, habituation, age, etc.

An individual and adaptive training is usually comparatively complicated and expensive. Particularly in the case of hearing aids, which represent highly individualized products, one teacher per user is usually needed for gaining familiarity with the product. Therefore, no qualitatively high-grade training possibilities are currently available for a broad range of users.

Conventionally, for example, training courses have been available on CD-ROM for hearing aid users. As already mentioned, however, this cannot be individualized training because several hearing aid users usually participate in the course.

SUMMARY OF THE INVENTION

An object of the present invention is to provide an individualized training procedure for hearing aid users.

This object is inventively achieved in a system for training hearing aid users, having a databank for storing a number of hearing training courses and a training device for acquiring a user profile and for implementing one of the hearing training courses according to the user profile, wherein the databank is connected to the training device via a data network.

The aforementioned object is also inventively achieved in a method for training hearing aid users by storing a number of hearing training courses in a databank, acquiring a user profile in a training device and implementing one of the hearing training courses according to the user profile, and transmitting the hearing training data from the databank to the training device and/or vice versa via a data network before or during the implementation of the hearing training.

Individual prerequisites and needs of the users can be taken into consideration in the inventive product training for hearing aids. Moreover, if the Internet is used as the data network, such Internet training courses are accessible to a broad range of users.

Further, the training can be adaptively designed. This means that it can be adapted to altered user requirements and outside boundary conditions, for example the technical possibilities, social circumstance and new perceptions.

A further advantage of the Internet-based training is that it is accessible at any time and everywhere. It can be implemented at a comparatively low price or free, and a certain anonymity can be assured. Training vie the Internet also enables multimedia presentations, which are frequently not available in training centers.

User experiences with respect to the respective product can be obtained in a customer survey in a return channel, for example via e-mail from the user to the manufacturer of hearing aids, and can be made available for further developments.

For the implementation of such individual and adaptive product training, training programs are first produced—offline—for the most important user profiles. For example, the user profiles take the experience of the users into consideration or how little time or what high expectations the users have. An account is set up for each product user who wishes to implement the training and a start profile is assigned on the basis of a first questionnaire. The current status of the training is stored after every log off, i.e. after every exit from the training system. Training thus can be continued at the same point at the next log-in, i.e. when the training system is used again. The progress of the training, which is reflected in the results of exercises and answers is continuously employed for reviewing the user profile and modifying it, if necessary.

DESCRIPTION OF THE DRAWINGS

The single FIGURE is a flowchart of the inventive, individually adaptive hearing training.

DESCRIPTION OF THE PREFERRED EMBODIMENTS

The following exemplary embodiment represents a preferred embodiment of the present invention.

The left side of the FIGURE illustrates the offline production of the various hearing training courses on the basis of specific user profiles. The right side of the FIGURE shows the on-line application of the hearing training.

The individual hearing training courses are stored offline in a databank 1. To this end, a representative selection of user profiles 2 is first generated. Subsequently, the hearing training courses 41 through **4*n* are produced (block 3) for the profiles 1 through n. The hearing training 41 for profile 1 contains exercises for speech comprehension and hearing tactics as well as technical advice. The hearing training 4*n*** for profile n contains, for example, advanced hearing exercises.

The user or hearing aid wearer then can individually use the hearing training courses stored in the databank 1 online. To this end, the user logs on in a step 5 to the training software made available in the Internet 6 with his/her password for authentication. The data of the user are registered in a brief interview 7, and an individual user profile is produced therefrom. For example, the user is asked about situations in which hearing difficulties occur. The allocation 8 of the individual user profile to one of the given user profiles stored in advance in the memory medium 2 subsequently ensues. The individual training 9 with the corresponding hearing training course downloaded in the databank 1 via the Internet then ensues on the basis of this allocation 8. The user profile is updated at the end of the training 9 before the user logs off in step 10 from the training software.

The updating or adaptation of the user profile ensues, for example, by documenting the course of the training in a databank 11 in the server that also serves as the databank 1 for the hearing training courses. Further individual data such as the age, the individual audiogram, the hearing aid being used and the like are stored in this databank 1. The training is thus implemented not only individually but also adaptively, matched to these conditions.

The databank 11 for storing the individual data alternatively can be located directly at the user. In this case, the individual data are communicated via the Internet to the server associated with the databank 1 before every training session, so that the databank 1 makes the appropriate hearing training available.

Although modifications and changes may be suggested by those skilled in the art, it is the intention of the inventors to embody within the patent warranted hereon all changes and modifications as reasonably and properly come within the scope of their contribution to the art.

We claim as our invention:

1. A system for individualized training of hearing aid users, comprising:

a databank in which a plurality of hearing training courses, respectively for a plurality of different hearing aid models are stored, each training course providing a different level of education for usage of one of said hearing aid models, said databank being accessible by a data network; and a training device also accessible via said data network that allows interaction with a hearing aid user of one of said hearing aid models, for acquiring a user profile of the hearing aid user, indicative of the level of education for usage suitable for the hearing aid user, and for selecting and providing one of said hearing training courses in said databank according to said user profile, said training device communicating with said databank via said data network said training device enabling a repeated acquisition of said user profile to acquire an updated user profile, and if said updated user profile is present, said training device implementing one of said hearing training courses stored in said databank dependent on said updated user profile.

2. A system as claimed in claim 1 wherein said data network is the Internet.

3. A system as claimed in claim 1 wherein said training device is a multimedia device for multimedia presentation of said hearing training course.

4. A system as claimed in claim 1 wherein said training device includes an authentication device for authentication of said hearing aid user.

5. A system as claimed in claim 1 wherein said training device contains a memory in which a plurality of predefined user profiles are stored, and wherein said training device comprises an allocation device for allocating said user profile to one of said predetermined user profiles.

6. A method for individualized training of hearing aid users, comprising the steps of:

storing a plurality of hearing training courses in a databank, respectively for a plurality of different hearing aid models, each training course providing a different level of education for usage of one of said hearing aid models;

by interaction by a user of one of said hearing aid models with a training device, acquiring a user profile for the user indicative of the level of education for usage suitable for the user;

establishing communication between said databank and said training device via a data network at a time selected from the group consisting of before a hearing training session and during a hearing training session;

dependent on said user profile, said training device selecting one of said hearing training courses from said databank according to said user profile and implementing said hearing training session using said one of said hearing training courses; and repeatedly acquiring said user profile with said training device, to obtain an updated user profile, and if said updated user profile is present, said training device selecting one of said hearing training courses dependent on said updated user profile.

7. A method as claimed in claim 6 comprising employing the Internet as said data network.

8. A method as claimed in claim 6 comprising the step of implementing said hearing training session as a multimedia presentation.

9. A method as claimed in claim 6 comprising the additional step of requiring a hearing aid user to provide authentication to said training device prior to said hearing training session.

10. A method as claimed in claim 6 comprising storing a plurality of predetermined user profiles and comparing said user profile to each of said predetermined profiles and allocating said user profile to one of said predetermined profiles dependent on said comparison.

11. A method as claimed in claim 10 comprising, for each of said predetermined user profiles, providing a hearing training course in said plurality of hearing training courses stored in said databank.

* * * * *